United States Patent
Gelvin et al.

(10) Patent No.: US 6,696,622 B1
(45) Date of Patent: Feb. 24, 2004

(54) ENHANCED PLANT CELL TRANSFORMATION BY ADDITION OF HOST GENES INVOLVED IN T-DNA INTEGRATION

(75) Inventors: Stanton B. Gelvin, West Lafayette, IN (US); Kirankumar S. Mysore, Ithaca, NY (US)

(73) Assignee: Purdue Research Foundation, West Lafayette, IN (US)

( * ) Notice: Subject to any disclaimer, the term of this patent is extended or adjusted under 35 U.S.C. 154(b) by 150 days.

(21) Appl. No.: 09/661,960

(22) Filed: Sep. 14, 2000

Related U.S. Application Data

(60) Provisional application No. 60/154,158, filed on Sep. 15, 1999.

(51) Int. Cl.$^7$ .................... C12N 15/82; C12N 15/74; C07H 21/04; A01H 5/00

(52) U.S. Cl. .................. 800/294; 800/306; 435/320.1; 536/23.6

(58) Field of Search ................. 536/23.1, 24.1, 536/23.6; 435/320.1, 419, 252.3; 800/295, 278, 294, 298, 306

(56) References Cited

FOREIGN PATENT DOCUMENTS

| DE | 43 09 203 C1 | 3/1993 |
|---|---|---|
| EP | 1 033 405 A2 | 9/2000 |
| WO | WO 97/12046 | 4/1997 |
| WO | WO 99/61619 | 12/1999 |
| WO | WO 00/17364 | 3/2000 |
| WO | PCT/US00/25260 | 4/2001 |

OTHER PUBLICATIONS

Gelvin, SB, Agrobacterium and Plant Genes Involved in T–DNA transfer and integration. Annu Rev. Plant Physiol. Plant Mol. Biol. 2000. 51: 223–56.*

Citovsky, V., et al. (1992) "Nuclear Localization of Agrobacterium VirE2 Protein in Plant Cells." *Science* 256: 1802–1805.

Hye Huh, G.H., et al. (1997) "Structural Characteristics of Two Wheat Histone H2A Genes Encoding Distinct Types of Variants and Functional Differences in their Promoter Activity." *Plant Molecular Biology* 33: 791–802.

Mysore, K.S., et al. (1998) "An Arabidopsis histone H3A mutant is deficient in Agrobacterium T–DNA integration." *PNAS* 97(2): 948–953.

Nakamura, Y., et al. (1998) "Structural Analysis of Arabidopsis Thaliana Chromosome." *Database EMBL (Online)*: Accession No: AB016878.

Nam, J., et al. (1999) "Identification of T–DNA Tagged Arabidopsis Mutants that are Resistant to Transformation by Agrobacterium."*Mol Gen Genet* 261: 429–438.

Prymakowska–Bosak, M., et al. (1996) "Histone H1 Overexpressed to High Level in Tobacco Affects Certain Developmental Programs but has Limited Effect on Basal Cellular Functions." *Proc. Natl. Acad. Sci. USA* 93: 10250–10255.

Regensburg–Tuink, A.J.G., et al. (1993) "Transgenic N. Glauca Plants Expressing Bacterial Virulence Gene virF are Converted into Hosts for Nopaline Strains of A. Tumefaciens." *Nature* 363: 69–71.

Ballas, N. and Citovsky, V. (1997) "Nuclear Localization Signal Binding Protein from Arabidopsis Mediates Nuclear Import of Agrobacterium VirD2 Protein." *Proc. Natl Acad Sci USA* 94: 10723–10728.

Britt, A.B. (1996) "DNA Damage and Repair in Plants." *Annu Rev Plant Physiol Plant Mol Biol* 47: 75–100.

Deng, W., et al. (1998) "Agrobacterium VirD2 Protein Interacts with Plant Host Cyclophilins." *Proc. Natl Acad Sci USA* 95: 7040–7045.

Ditta, G., et al. (1980) "Broad host Range DNA Cloning System for Gram–Negative Bacteria: Construction of a Gene Bank of *Rhizobium Meliloti.*" *Proc Natl Acad Sci USA* 77(12): 7347–7351.

Gheysen, G, et al. (1991) "Illegitimate Recombination in Plants: A Model for T–DNA Integration." *Genes & Development* 5: 287–297.

Jefferson, R.A., et al. (1987) "GUS Fusions: β–Glucuronidase as a Sensitive and Vesatile Gene Fusion Marker in Higher Plants." *EMBO J* 6(13): 3901–3907.

Koncz, C. and Schell, J. (1986) "The Promoter of $T_L$–DNA Gene 5 Controls the Tissue–Specific Expression of Chimeric Genes Carried by a Novel Type of Agrobacterium Binary Vector." *Mol Gen Genet* 204: 383–396.

Lichtenstein, G., and Draper, J., (1986) "Genetic of Engineering Plants." In Glover, D.M. (ed.) *DNA Cloning: A Practical Approach* 2: 67–119 (IRL Press, Oxford).

(List continued on next page.)

*Primary Examiner*—Phuong T. Bui
*Assistant Examiner*—Georgia Helmer
(74) *Attorney, Agent, or Firm*—Alice O. Martin; Barnes & Thornburg

(57) ABSTRACT

Adding at least one gene involved in plant host cell T-DNA integration enhances transformation by Agrobacterium. The histone H2A gene encoded by the Arabidopsis RAT5 gene increases transformation frequencies of plants, most likely by causing overexpression of a product needed for T-DNA integration. Agrobacterium tumefaciens genetically transforms plant cells by transferring a portion of the bacterial Ti-plasmid, designated the T-DNA, to the plant, and integrating the T-DNA into the plant genome. However, not all plants are transformable by Agrobacterium and transformation frequencies may be too low to be useful. Little is known about the T-DNA integration process, and no plant genes involved in integration have been identified prior to the present invention.

3 Claims, 8 Drawing Sheets

OTHER PUBLICATIONS

Matsumoto, S., et al. (1990) "Integration of Agrobacterium T–DNA into a Tobacco Chromosome Possible Involvement of DNA Homology between T–DNA and Plant DNA." *Mol Gen Genet* 224: 309–316.

Mysore, K.S., et al. (1998) "Role of the *Agrobacterium Tumefaciens* VirD2 Protein in T–DNA Transfer and Integration." *American Phytopathological Society* 11(7): 668–683.

Nam, J., et al. (1997) "Difference in Susceptibility of Arabidopsis Ecotypes to Crown Gall Disease May Result from a Deficiency in T–DNA Integration." *Plant Cell* 9: 317–333.

Narasimhulu, S.B., et al. (1996) "Early Transcription of Agrobacterium T–DNA Genes in Tobacco and Maize." *Plant Cell* 8: 873–886.

Ni, M., et al., (1995) "Strength and Tissue Specificity of Chimeric Promoters Derived from the Octopine and Mannopine Synthase Genes." *Plant J.* 7(4): 661–676.

Offringa, R., et al. (1990) "Extrachromosomal Homologous Recombination and Gene Targeting in Plant Cells after Agrobacterium Mediated Transformation." *EMBO J* 9(10): 3077–3084.

Ohba, T., et al. (1995) "DNA Rearrangement Associated with the Integration of T–DNA in Tobacco: An Example for Multiple Duplications of DNA Around the Integration Target." *Plant J* 7(1): 157–164.

Paszkowski, J., et al. (1988) "Gene Targeting in Plants." *EMBO J* 7(13): 4021–4026.

Sambrook, M.A., et al. (1982) in *Molecular Cloning: A Laboratory Manuel*. $1^{st}$ ed. Cold Spring Harbor Laboratory Press, Cold Spring Harbor, New York, pp. 150–172; 312–328, 365–381 and 383–389.

Sheng, J. and Citovsky, V. (1996) "Agrobacterium–Plant Cell DNA Transport: Have Virulence Proteins, Will Travel." *Plant Cell* 8: 1699–1710.

Zupan, J. and Zambryski, P. (1997) "The Agrobacterium DNA Transfer Complex." *Critical Reviews in Plant Sciences* 16(3): 279–295.

Bent, Andrew F. and Clough, Steven J. (1998) "Agrobacterium Germ–Line Transformation: Transformation of Arabidopsis without Tissue Culture" *Plant Molecular Biology Manual* B7:1–14.

* cited by examiner

F1 (Ws x rat5)

Fig. 1B

```
TCAAAGGAAAGACATTAAATTAGAAATTTGAAACATGTTGATAGATCATGTCCTTCTTCTGGGTTACCCAGTT    80
TTGCCCCTAAAACCTAAAACCAACAGGACCATCATTTCGACCACCACCACCATTGACTGGTCTGCCCAATCTAGCTATGATA   160
TATCTTAATTCCGTATGACTTGGATCCATAAATATTGAAATAGATTTGGTGAACACAAATTACTCTTAAAACTTCTCT   240
CTTTCATGCATGTTCTTTTTCCACTTTAACATTTTATATAGTGACATTTTAGTAATCCAACGTTATTTATATGATTA   320
GTAATTCATCAAATTTATATAGTGATAAAATTCCACAATGGTTGTTCAATAAAAATATGAACACAACAATAGAATTAGTA   400
AAAGTGACTATGTTAAATCATTTCTTCGCTTGGGGTTTGGTGGGCGAGTTCTAAACCATAAGCGGCCCATTACTTCGT   480
AAACTCAATTCGATTTGTTCAGCGTTCCAAGCGTTCCAGAGAAACCAACAGCCCATAATATATTTCAAGGGCATAAATAAATTGAGGTTATATGGA   560
AAATTTGGAAATTCCCTCGTCCAGAGAAACCAACAGTTTAAACCTGATCGCGTACTCTATTCCTATGGTCAAATAACTTAA   640
GTAGCCATTCATTAATTATATACAACAATCAGATTTCTCTCGTTAATTCGTCAAGAAAAATTCGATTTTTTGGCTCTTTG   720
TCCTCCACATATATAACACAATCAGATTTCTCTCGTTAATTCGTCAAGAAAAATTCGATTTTTTGGCTCTTTG   800
TGGGTTGTTGTGAAAATGGCTGGTCGTGGGTCGTATCGCTCGTTCTTAAAGCGCGGTAAATACGCCGAACGTGTTGGTGCC   880
GCAAAGCCGGTCTTCAATTCCCGGTGGGTCGTATCGCTCGTTCTTAAAGCGCGGTAAATACGCCGAACGTGTTGGTGCC   960
GGTGCTCCGGTTTATCTCGCGCCCCGTTCTCGACTCTGTCTGACTCTGTTTGCGTGATATTTGGCCGCCGAGGTAAATTACATCGTCTTTTCTCTTTCCCA  1040
TTCCGTTCCGATCTTATTCGTCTGACTCTGTTTGCGTGATCGATTACGAATCTAGGTTCTCTTACATTTTCCGAATTT  1120
GACATGCAAAAATTGAATTAGATTCGTGTTTGAATTGAATTGTGTAGTTCTGTAATGAACCTAATTTTTTCAATTATGGTAAC  1200
GATTGGTGATGGTAATCGAGATCATATGAATCGTTGTAGTTTCTCGCAAGATTCTAAATTTTTTCAATTATGGTAAC  1280
CAATTGATTTGAGTTGTTAAAGTTCTAAATTGGAAAAGTTTGATCATGAATTGTGTTTGTTTTGAATTTGTTCAGGTTCT  1360
TGAATTAGCTGGAAACGCAGCAAGAGACAAGAAGACAACAAGACACGTATTGTTCCTCGTCACATTGTTCCTCGTCACATTCAGCTTGCCGTCAGAAACG  1440
ATGAGGAGCTAAGCAAGCTTCTTGGAGATGTGACGATTGCTAATGCCTAACATCCAACATCCACAATCTCCTTCTC  1520
CCTAAGAAGGCTGGTGCTTCAAAGCCCTCAGGAAGATTAGGTCTTTTAACACAATGATATAGAACACGTCTCTTTTGCA  1600
TTTTTCAGGATATATGTGGTGTAAACAAATTGACGCTTAGACAACTTAATAACACATTGCGAGCGTTTTAATGTACTG  1680
AATT (SEQ ID NO: 1)
```

T-DNA insertion site

Italics → Open reading frame
Bold → Intron
Underline → T-DNA LB sequence

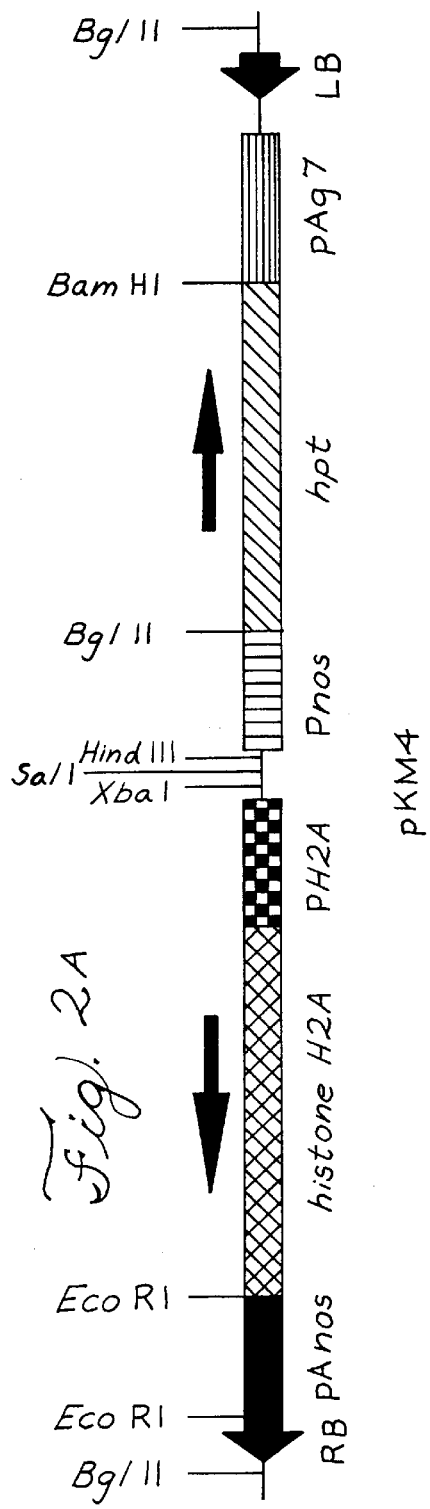
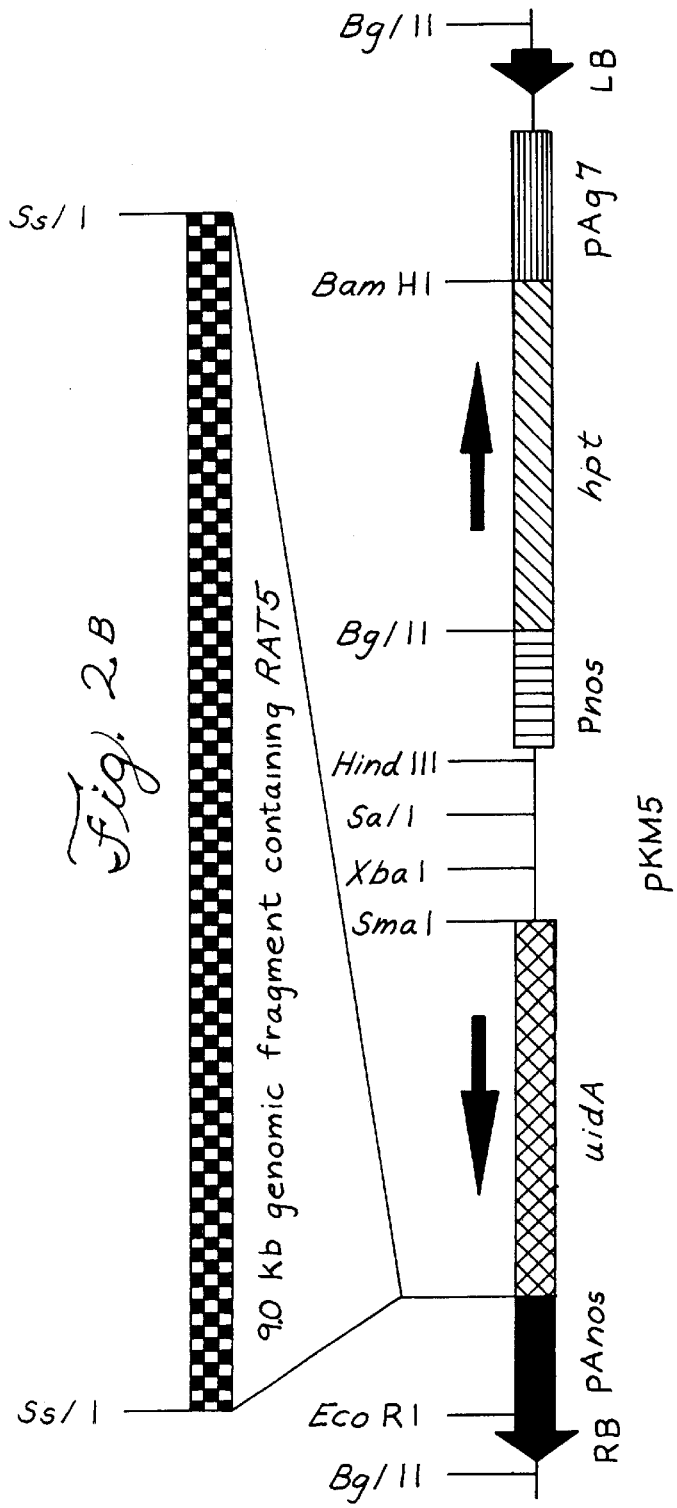
Fig. 2A
Fig. 2B

Transgenic rat5 plants expressing
the RAT5 histone H2A gene

Transgenic Ws plants overexpressing the *RAT5* histone H2A gene

| rat5 | Ws | rat5 | Ws |

23 kbp → gusA Gene    PAL Gene

SEQUENCE LISTING

<160> NUMBER OF SEQ ID NOS: 1

<210> SEQ ID NO 1
<211> LENGTH: 1684
<212> TYPE: DNA
<213> ORGANISM: Arabidopsis sp.

<400> SEQUENCE: 1

-continued

```
tcaaaggaa agacattaaa ttagaaattg aattttgaaa catgttgata gatcatgtcc      60
ttcttctggg ttacccagtt ttgccctaaa acctaaaacc aacaggacca tcatttcgac    120
cacaccacat tgactggtct gccccaatct agctatgata tatcttaatt tccgtatgac    180
ttggatccat aaatattgaa atagatttgg tgaacacaaa ttactcttaa aacttcttct    240
ctttcatgca tgttctttt ctcactttaa cattttata tagtgacatt tttagtaatc     300
caacgttatt tatatgatta gtaattcatc aaatttatat agtgataaaa ttccacaatg    360
gttgttcaat aaaaatatga acaacacaat agaattagta aaagtgacta tgttaaatca    420
ttttcttcgc tggggtttgg tgggcgagtt ctaaacccat aagcggccca tttacttcgt    480
aaactcaatt cgatttgttc agcgttccaa gcccataata ttattttcaa gggcataaaa    540
taaattgagg tttatatgga aaatttggaa attccctcgt ccagaagaaa ccaacaaaaa    600
actgcaaaag ttcaagcggt gggagaaaaa acttcagatc gtagccattc attaaattat    660
aatcaacggt ttaaacctct tcgatccgcg tactctattc cttatggtca aataacttaa    720
tcctccacat atataacaac aatcagattt ctctctgtta atttcgtcaa gaaaaaatt    780
cgattttttt gcgctctttg tgggttgttg ttgttgaaaa tggctggtcg tggaaaaact    840
cttggatccg gtggggcgaa gaaagctaca tctcggagta gcaaagccgg tcttcaattc    900
ccggtgggtc gtatcgctcg tttcttaaaa gccggtaaat acgccgaacg tgttggtgcc    960
ggtgctccgg tttatctcgc cgccgttctc gaatatttgg ccgccgaggt aaaattacat   1020
cgtcttttct ctctttccca ttccgtttcc gatcttattc gtctgactct gttttttgcgt  1080
gatcgattac gaatctaggg ttcttacatt ttccgaattt gacatgcaaa aattgaatta   1140
gattcgtgtt tgaattgaat tgttgtagtt ctgtaattga cctaattttg ggtttgttct   1200
gattggttga tggtaatcga gatcatatga atcgttgtag ttttctcgca agattctaaa   1260
ttttttcaa ttatggtaac caatttgatt tgagttgtta aagttctcaa atttggaaag   1320
tttgatcatg aattgtgtgt tttgaatttg ttcaggttct tgaattagct ggaaacgcag    1380
caagagacaa caagaagaca cgtattgttc ctcgtcacat tcagcttgcg gtcagaaacg   1440
atgaggagct aagcaagctt cttggagatg tgacgattgc taatggagga gtgatgccta    1500
acatccacaa tctccttctc cctaagaagg ctggtgcttc aaagcctcag gaagattagg   1560
tcttttaaca caatgatata gaacacgtct ctcttttgca tttttcagga tatattgtgg   1620
tgtaaacaaa ttgacgctta gacaacttaa taacacattg cggacgtttt taatgtactg   1680
aatt                                                                 1684
```

ENHANCED PLANT CELL TRANSFORMATION BY ADDITION OF HOST GENES INVOLVED IN T-DNA INTEGRATION

This application claims priority to U.S. provisional application serial no. 60/154,158 filed Sep. 15, 1999.

The U.S. government may have rights in this invention due to partial support from the National Science Foundation (IBN-9630779).

BACKGROUND

The invention relates enhanced Agrobacterium transformation frequencies of plants due to overexpression of the histone H2A gene encoded by the Arabidopsis RAT5 gene. *Agrobacterium tumefaciens* is a gram negative soil bacterium that has been exploited by plant biologists to introduce foreign DNA into plants. However, there are some limitations on the use of this transforming vector, e.g. difficulties in transforming monocots, and transforming frequencies may be too low to be useful. Although known for this practical application, the actual mechanism of DNA transfer from bacteria to plants is not completely understood.

*Agrobacterium tumefaciens* genetically transforms plant cells by transferring a portion of the bacterial Ti-plasmid, designated the T-DNA, to the plant, and integrating the T-DNA into the plant genome. Little is known about the T-DNA integration process, and no plant genes involved in integration have previously been identified. The DNA that is transferred from Agrobacterium to the plant cell is a segment of the Ti, or tumor inducing, plasmid called the T-DNA (transferred DNA). Virulence (vir) genes responsible for T-DNA processing and transfer are reported to lie elsewhere on the Ti plasmid. The role of vir genes in T-DNA processing, the formation of bacterial channels for export of T-DNA, and the attachment of bacteria to the plant cell are reported (Sheng and Citovsky, 1996; Zupan and Zambryski, 1997). In contrast, little is known about the role of plant factors in T-DNA transfer and integration. The isolation of a putative plant factor has recently been reported. Ballas and Citovsky showed that a plant karyopherin α (AtKAP α) can interact with VirD2 nuclear localization sequences in a yeast two-hybrid interaction system, and is presumably involved in nuclear translocation of the T-complex. Using a similar approach, a tomato type 2C protein phosphatase, DIG3, that can interact with the VirD2 NLS was identified. Unlike AtKAP α, DIG3 plays a negative role in nuclear import. After the T-DNA/T-complex enters the nucleus, it must integrate into the plant chromosome. Plant chromosomal DNA is packaged into nucleosomes consisting primarily of histone proteins. The incoming T-DNA may have to interact with this nucleosome structure during the integration process. However, T-DNA may preferentially integrate into transcribed regions of the genome. These regions are believed to be temporarily free of histones. How exactly T-DNA integration takes place is unknown. Recent reports have implicated involvement of VirD2 protein in the T-DNA integration process. Plant proteins are also likely to be involved in this process (Deng et al., 1998; Ballas and Citovsky, 1997; Tao, et al.). Other evidence for the involvement of plant factors in T-DNA transfer and integration comes from identification of several ecotypes of Arabidopsis that are resistant to Agrobacterium transformation.

To identify plant genes involved in Agrobacterium-mediated transformation, a T-DNA tagged Arabidopsis library was screened for mutants that are resistant to Agrobacterium transformation (rat mutants). There are several steps in which plant genes are likely involved in the Agrobacterium-mediated transformation process. First, plant-encoded factors could be involved in the initial step of bacterial attachment to the plant cell surface. Mutants and ecotypes that are deficient in bacterial attachment have been identified and genes involved in bacterial attachment are currently being characterized. The next step in which a plant factor(s) could be involved is the transfer of T-strands from the bacteria to plant cells across the plant cell wall and membrane. After T-DNA/T-complex enters the cytoplasm of the plant cell, plant factors are required to transport the T-complex to the nucleus.

An Arabidopsis T-DNA tagged mutant, rat5, was characterized that is deficient in T-DNA integration and is resistant to Agrobacterium-mediated root transformation. Both genetic and DNA blot analyses indicated that there are two copies of T-DNA integrated as a tandem repeat at a single locus in rat5. No major rearrangements are in the rat5 plant DNA immediately surrounding the T-DNA insertion site. These data strongly suggest that in rat5 the T-DNA had inserted into a gene necessary for Agrobacterium-mediated transformation. The sequence of the T-DNA left border-plant junction indicated that the T-DNA had inserted into the 3' untranslated region of a histone H2A gene. This insertion is upstream of the consensus polyadenylation signal. By screening an Arabidopsis ecotype Ws cDNA library and sequencing 20 different histone H2A cDNA clones, and by performing a computer data base search, at least six different histone H2A genes were shown. These genes encode proteins that are greater than 90% identical at the amino acid sequence level. Thus, the histone H2A genes comprise a small multi-gene family in Arabidopsis.

T-DNA integration does not appear to take place by homologous recombination, believed to be the most common method of foreign DNA integration in prokaryotes and lower eukaryotes, because no extensive homology between the T-DNA and target sequences has been found. T-DNA is reported to integrate by illegitimate recombination (Matsumoto el al., 1990; Gheysen et al., 1991; Mayerhofer et al., 1991; Ohba et al., 1995). Illegitimate recombination is the predominant mechanism of DNA integration into the genomes of higher plants (Britt, 1996; Offringa et al., 1990; Paszkowski et al., 1988).

Information on factors affecting Agrobacterium transformation frequencies in plants is needed to improve performance of this method.

SUMMARY OF THE INVENTION

The invention relates to increased Agrobacterium transformation frequencies in plants due to addition of at least one gene involved in host T-DNA integration, to the host plant. In an embodiment, addition of at least one histone H2A gene encoded by the Arabidopsis RAT5 gene enhances transformation frequencies, most likely due to overexpressing of histone as compound to the host's natural expression levels. The gene can be either in transgenic plants or carried by the transforming agent, T-DNA for practice of the invention.

Overexpression of histone genes of the present invention overcomes the poor performance that limits the use of Agrobacterium as a transforming vector. Many plants can be transformed transiently by Agrobacterium so they express the transforming gene for a period of time, but are not stably transformed because of T-DNA integration problems. Therefore, transgenic plants are not produced. The gene H2A (RAT5) plays an important role in illegitimate recombination of T-DNA into the plant genome and the gene's overexpression enhances transformation.

Transient and stable GUS (β-glucuronidase) expression data and the assessment of the amount of T-DNA integrated into the genomes of wild-type and rat5 Arabidopsis plants indicated that the rat5 mutant is deficient in T-DNA integration needed for transformation. Complementing the rat5 mutation was accomplished by expressing the wild-type RAT5 histone H2A gene in the mutant plant. Surprisingly, overexpression of RAT5 in wild-type plants increased Agrobacterium transformation efficiency. Furthermore, transient expression of a RAT5 gene from the incoming T-DNA was sufficient to complement the rat5 mutant and to increase the transformation efficiency of wild-type Arabidopsis plants. The present invention provides methods and compositions to increase stable transformation frequency in plants using direct involvement of a plant histone gene in T-DNA integration.

DESCRIPTION OF THE INVENTION

Several T-DNA tagged [plants which genes have randomly been disrupted by integration of a T-DNA] mutants of Arabidopsis were identified that are recalcitrant to Agrobacterium root transformation. These are called rat mutants (resistant to Agrobacterium transformation). In most of these mutants Agrobacterium transformation is blocked at an early step, either during bacterial attachment to the plant cell or prior to T-DNA nuclear import. In some of the mutants, however, the T-DNA integration step is most likely blocked. Because plant factors involved in illegitimate recombination of T-DNA into the plant genome have not previously been identified, the characterization of a T-DNA tagged Arabidopsiy mutant, rat5, that is deficient in T-DNA integration, is an aspect of the present invention.

Figure 1A:
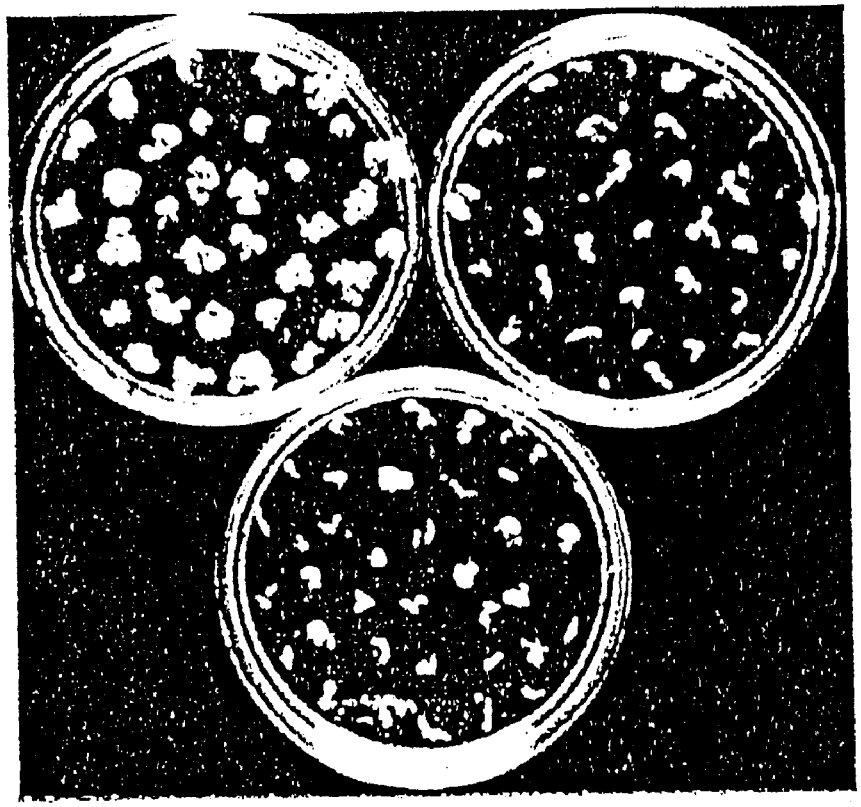
FIG. 1 shows characteristics of the rat5 mutant: (A) stable transformation of wild-type Arabidopsis ecotype Ws, the rat5 mutant, and the F1 progeny; (B) sequence of the rat5/T-DNA junction region; (C) pattern of T-DNA integration in rat5: LB, T-DNA left border; RB, T-DNA right border; pBR322, pBR322 sequences containing the β-lactamase gene and ColE1 origin of replication; Tn903, kanamycin resistance gene for *E. coli* selection; Tn5, kanamycin resistance gene for plant selection.

Characterization of the rat5 mutant. rat5, an Arabidopsis T-DNA tagged mutant, was previously identified as resistant to Agrobacterium root transformation. An in vitro root inoculation assay was performed using the wild-type Agrobacterium strain A208 (At10). After one month, the percentage of root bundles that formed tumors was calculated. Greater than 90% of the root bundles of the wild-type plants (ecotype Ws) formed large green teratomas. In contrast, fewer than 10% of the root bundles from the rat5 plants responded to infection, forming small yellow calli (FIG. 1A). A homozygous rat5 plant (pollen donor) was crossed to a wild-type plant (egg donor) and the resulting F1 progeny tested for susceptibility to Agrobacterium transformation. This analysis indicated that rat5 is a dominant mutation (7; FIG. 1A). Further analysis of F2 progeny indicated that kanamycin resistance segregated 3:1, indicating that a single locus had been disrupted by the mutagenizing T-DNA. Kanamycin resistance co-segregated with the rat5 phenotype, indicating that a gene involved in Agrobacterium transformation had most likely been mutated by the T-DNA insertion.

Figure 1C:
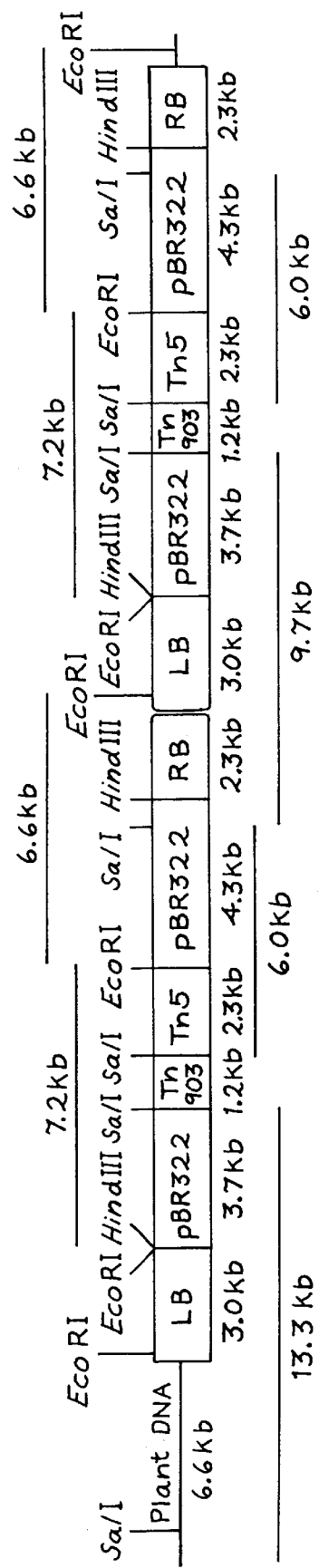

Recovery of a T-DNA-plant junction from rat5. The T-DNA integration pattern in the rat5 mutant was determined by DNA blot analyses. The results indicated that there are only two copies of the mutagenizing T-DNA integrated into the genome of the rat5 mutant. Further analysis indicated that these two T-DNA copies are present as a direct tandem repeat, as shown in FIG. 1C.

A left border (LB) T-DNA-plant junction was recovered from rat5 using a plasmid rescue technique (see Materials and Methods) and a restriction endonuclease map of this T-DNA-plant junction was constructed. An approximately 1.7 kbp EcoRI fragment that contains both plant and LB DNA was subcloned into pBluescript and subsequently sequenced at the Purdue University sequencing center. The sequence of this fragment is shown in FIG. 1B. DNA sequence analysis of this junction region indicated that the T-DNA had inserted into the 3' untranslated region (UTR) of a histone H2A gene (FIG. 1B). The histone H2A genes of Arabidopsis were further characterized by isolating and sequencing numerous cDNA and genomic clones. Six different gene variants of histone H2A were identified, indicating that the histone H2A genes of Arabidopsis comprise a small multi-gene family. In a lambda genomic DNA library a clone was identified containing the wild-type histone H2A gene corresponding to RAT5. DNA sequence analysis of this genomic clone indicated that in rat5 the T-DNA had inserted upstream of the consensus polyadenylation signal (AATAA). DNA blot analysis of Ws and rat5 DNA indicated that the T-DNA insertion in rat5 did not cause any major rearrangements in the plant DNA immediately around the site of insertion. Disruption of the 3' UTR of the RAT5 histone H2A gene is likely the sole cause for the rat phenotype in the rat5 mutant.

FIG. 1 shows characterization of the rat5 mutant. (A) Stable transformation of wild-type Arabidopsis ecotype Ws, the rat5 mutant, and the F1 progeny. Sterile root segments were infected with *A. tumefaciens* A208. Two days after cocultivation, the roots were transferred to MS medium lacking phytohormones and containing timentin as an antibiotic. Tumors were scored after four weeks. (B) Sequence of the rat5/T-DNA junction region. (C) Pattern of T-DNA integration in rat5. LB, T-DNA left border; RB, T-DNA right border; pBR322, pBR322 sequences containing the β-lactamase gene and ColE1 origin of replication; Tn903, kanamycin resistance gene for *E. coli* selection; Tn5, kanamycin resistance gene for plant selection. Five μg of genomic DNA from the rat5 mutant was digested with either EcoRI or SalI and was blotted onto a nylon membrane. An EcoRI-SalI fragment of pBR322 was used as the hybridization probe. Restriction fragment sizes shown above the T-DNA were detected by EcoRI digestion and the sizes shown below the T-DNA were detected by SalI digestion.

Figure 2C:
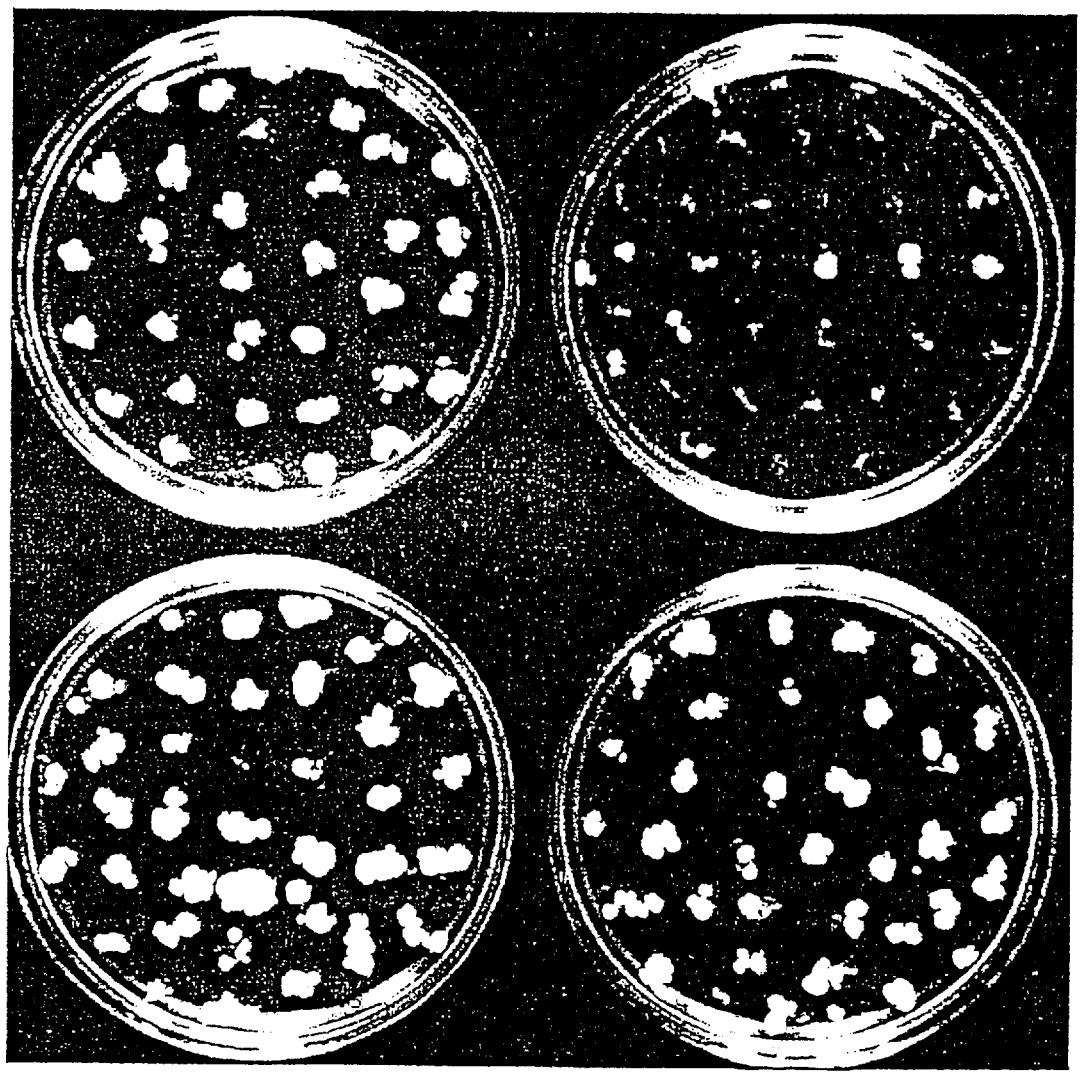
FIG. 2 shows complementation of the rat5 mutant and overexpression of RAT5 in wild-type Arabidopsis plants; maps of the binary vectors pKM4 (A) and pKM5 (B) RB, T-DNA right border; LB, T-DNA left border; pAnos, nopaline synthase polyadenylation signal sequence; histone H2A, coding sequence of the RAT5 histone H2A gene; pH2A, promoter sequence of the RAT5 histone H2A gene; Pnos, nopaline synthase promoter; hpt, hygromycin resistance gene; pAg7, agropine synthase polyadenylation signal sequence; uidA, promoterless gusA gene; arrows above the histone H2A, uidA, and hpt genes indicate the direction of transcription; (C) complementation of the rat5 mutant; (D) tumorigenesis assay of Ws transgenic plants overexpressing the RAT5 histone H2A gene.

Complementation of the rat5 mutant with a wild-type histone H2A gene (RAT5). Two different constructions were made to perform a complementation analysis of the rat5 mutant. First, a nopaline synthase terminator (3' NOS) was fused to the 3' region of the 1.7 kbp junction fragment (the sequence of this 1.7 kbp fragment is shown in FIG. 1B). This construction contains the RAT5 histone H2A gene with its own promoter and a 3' NOS. This fragment (RAT5 plus 3' NOS) was cloned into the binary vector pGTV-HPT of beaker containing a hygromycin resistance gene between the left and the right T-DNA borders, resulting in the binary vector pKM4 (FIG. 2A). For the second construction, a 9.0 kbp SacI genomic fragment of wild-type Ws DNA containing a histone H2A gene (RAT5) plus at least 2.0 kbp sequences upstream and downstream of RAT5 was cloned into the binary vector pGTV-HPT, resulting in the binary vector pKM5 (FIG. 2B). pKM4 and pKM5 were transferred separately into the non-tumorigenic Agrobacterium strain GV3101, resulting in strains *A. tumefaciens* At1012 and At1062, respectively.

Both strains At1012 and At1062 were separately used to transform rat5 plants using a germ-line transformation method (Bent et al., 1998) and transgenic rat5 plants were selected for resistance to hygromicin (20 $\mu$g/ml). Several transgenic plants (T1) were obtained. These transgenic plants were allowed to self fertilize and T1 seeds were collected. Six transgenic lines obtained by transformation with At1012 (the wild-type histone H2A with 3' NOS) were randomly selected and their seeds were germinated in the presence of hygromycin. Tumorigenesis assays were performed as described in Nam et al. (1999) using *A. tumefaciens* At10 and a sterile root inoculation protocol, on at least five different plants from each of the six transgenic lines. The results indicated that in five of the six transgenic rat5 lines tested, the tumorigenesis-susceptibility phenotype was recovered (FIG. 2C; Table 1). Teratomas incited on the roots of these plants appeared similar to tumors generated on a wild-type plant. One of the transgenic plants tested did not recover the tumorigenesis-susceptibility phenotype, probably because of an inactive transgene. Transgenic T1 plants of rat5 obtained by transformation with At1062 (containing a genomic encoding RAT5 from the wild-type plant) were also tested for restoration of the tumorigenesis-susceptibility phenotype. Some of these plants were also able to recover the tumorigenesis-susceptibility phenotype, indicating complementation of the rat5 mutation. Hygromycin-resistant transgenic plants generated by transforming the rat5 mutant with pGPTV-HPT alone did not form tumors upon infection with *A. tumefaciens* A208.

To confirm the genetic basis of the complementation experiment, a co-segregation analysis was performed on one of the rat5 transgenic lines (rat5 At1012-6) obtained by transformation of the rat5 mutant with *A. tumefaciens* At1012. To examine the co-segregation of the complementing T-DNA containing the wild-type RAT5 gene with the tumorigenesis-susceptibility phenotype, seeds from a T2 plant homozygous for the rat5 mutation but heterozygous for hygromycin resistance were germinated and grown on B5 medium without selection. Roots of these plants were subsequently tested for hygromycin-resistance and susceptibility to crown gall tumorigenesis. All plants that were sensitive to hygromycin were also resistant to tumor formation in a manner similar to that of the rat5 mutant. Of the 25 hygromycin-resistant plants, at least 8 were susceptible to tumorigenesis. However, 17 hygromycin-resistant plants remained recalcitrant to Agrobacterium-mediated transformation. It is likely that these plants are heterozygous with respect to the complementing RAT5 gene and did not express this gene to a level high enough to restore susceptibility to tumorigenesis. This possibility corresponds to the finding that the rat5 mutation is dominant, and that therefore one active copy of RAT5 is not sufficient to permit Agrobacterium-mediated transformation. Taken together, the molecular and genetic data strongly indicate that in the rat5 mutant disruption of a histone H2A gene is responsible for the tumorigenesis-deficiency (rat) phenotype.

Figure 2D:
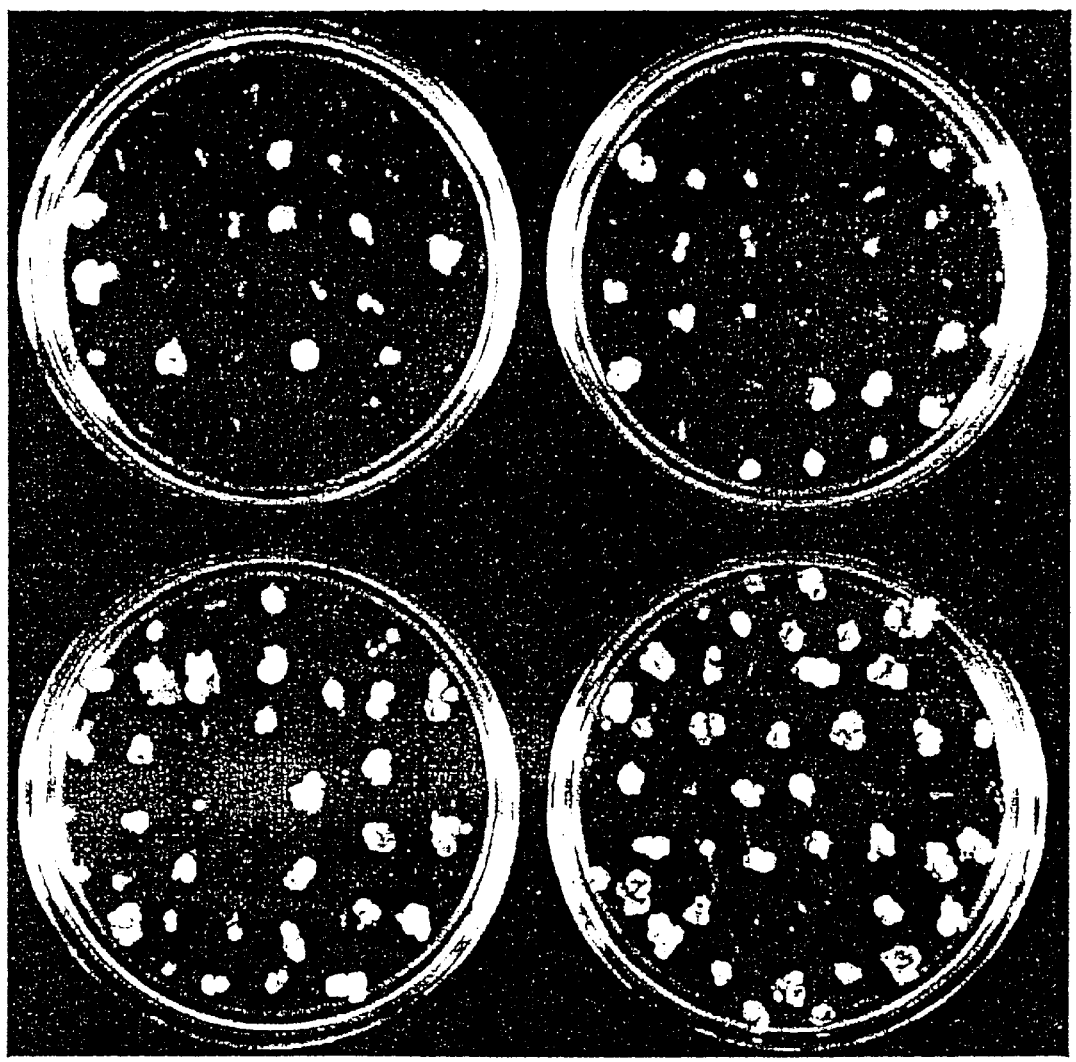

Overexpression of a histone H2A (RAT5) gene in wild-type plants improves the efficiency of Agrobacterium transformation. To determine further whether the RAT5 gene plays a direct role in Agrobacterium-mediated transformation, *A. tumefaciens* At1012 was used to generate several transgenic Arabidopsis plants (ecotype Ws) containing additional copies of the RAT5 histone H2A gene. These transgenic plants were allowed to self-pollinate, T1 seeds were collected, and T2 plants were germinated in the presence of hygromycin. Tumorigenesis assays were performed as described herein at least five plants from each of four different transgenic lines. Because ecotype Ws normally is highly susceptible to Agrobacterium transformation, the tumorigenesis assay was altered to detect any subtle differences between the transformation-susceptible wild-type plant and transgenic wild-type plants overexpressing RAT5. These alterations included inoculation of root segments with a 100-fold lower concentration ($2 \times 10^7$ cfu/ml) of bacteria than that normally used ($2 \times 10^9$ cfu/ml), and spreading individual root segments rather than bundles of root segments on MS medium to observe tumor production. The results, shown in Table 1 and FIG. 2D, indicate that transgenic plants overexpressing RAT5 are approximately twice as susceptible to root transformation as are wild-type Ws plants. These data indicate that the RAT5 histone H2A gene plays a direct role in T-DNA transformation, and that overexpression of RAT5 can increase susceptibility to transformation.

Transient expression of histone H2A is sufficient to permit transformation of rat5 and to increase the transformation efficiency of wild-type Ws plants. Expression of the RAT5 histone H2A gene from the incoming T-DNA complement the rat5 mutant. Although transformation of this mutant with an Agrobacterium strain harboring PGPTV-HYG (lacking a histone H2A gene) resulted in only a few, slow-growing calli on hygromycin selection medium, Agrobacterium strains harboring pKM4 or pKM5 incited rapidly growing hygromycin-resistant calli on 60±21% and 54±22% of the rat5 root segment bundles, respectively. In addition, when wild-type plants were infected (at low bacterial density) with a tumorigenic Agrobacterium strain (A208) harboring pKM4, 78±8% of the root segments developed tumors, compared to 36±9% of the root segments infected with a tumorigenic bacterial strain harboring pGPTV-HYG. These transformation experiments indicate that Agrobacterium strains containing the binary vectors pKM4 or pKM5 are able to transform rat5 mutant plants at relatively high efficiency, and on wild-type plants are two-fold more tumorigenic, and are better able to incite hygromycin-resistant calli, than are Agrobacterium strains containing the "empty" binary vector pGPTV-HYG. Transiently produced histone H2A may improve the stable transformation efficiency of plants by Agrobacterium.

Figure 3A:
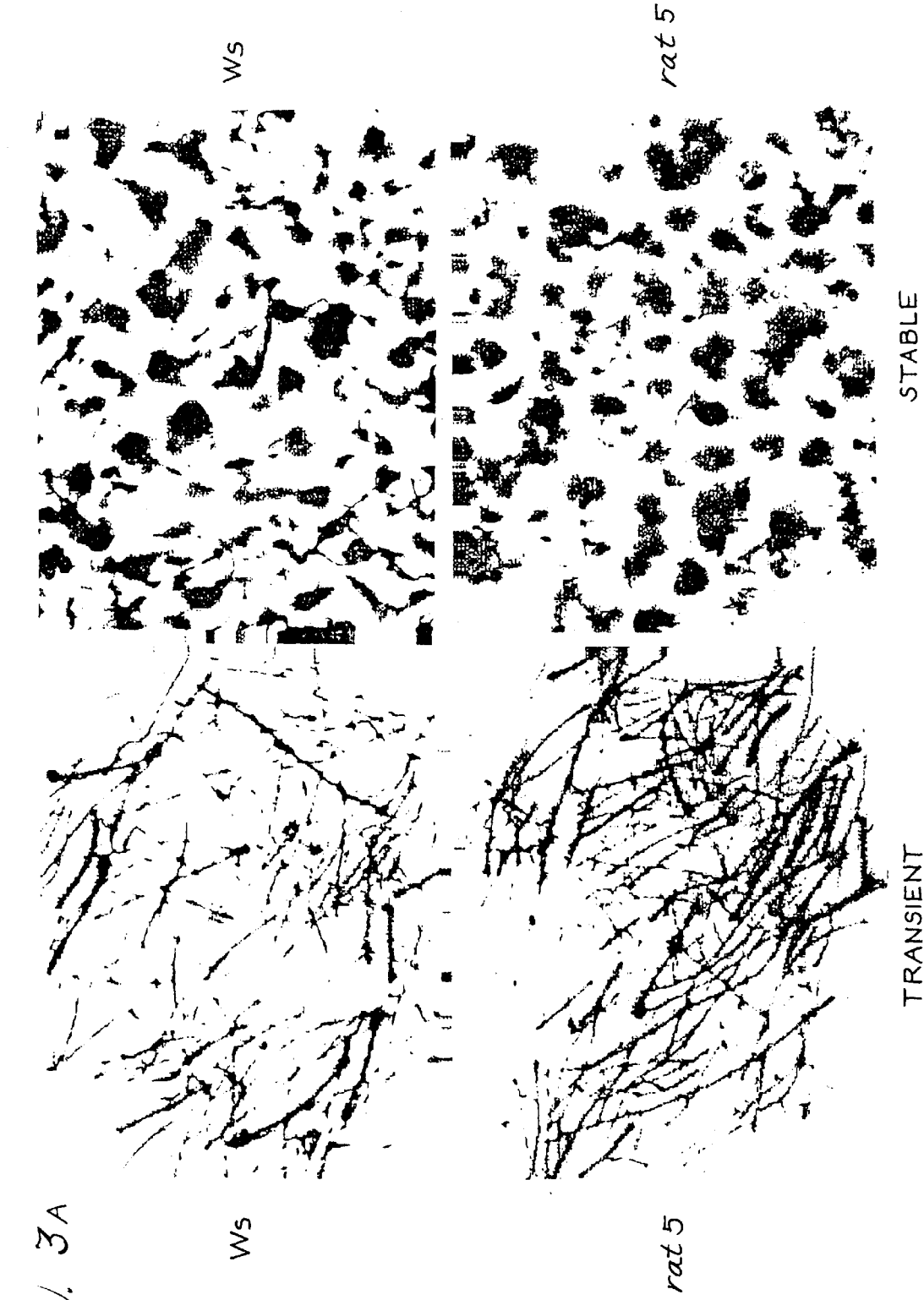
FIG. 3 shows T-DNA integration assays of rat5 and Ws plants; (A) transient and stable GUS expression in Ws and rat5 ; (B) T-DNA integration in rat5 and Ws plants.

The rat5 mutant is deficient in T-DNA integration. Agrobacterium-mediated transformation of the Arabidopsis rat5 mutant results in a high efficiency of transient transformation but a low efficiency of stable transformation, as determined by the expression of a gusA gene encoded by the T-DNA. This result suggested that rat5 is most likely deficient in T-DNA integration. To test this hypothesis directly root segments from Ws and rat5 plants were inoculated with *A. tumefaciens* GV3101 harboring the T-DNA binary vector pBISN1. pBISN1 contains a gusA-intron gene under the control of a "super-promoter" (Ni et al., 1995; Narasimhulu et al., 1996). Two days after cocultivation, the root segments were transferred to callus inducing medium containing timentin (100 μg/ml) to kill the bacteria. Three days after infection, a few segments were stained for GUS activity using the chromogenic dye X-gluc. Both the wild-type and the rat5 mutant showed high levels of GUS expression (approximately 90% of the root segments stained blue; FIG. 3A). The remaining root segments were allowed to form calli on callus inducing medium containing timentin to kill Agrobacterium, but lacking any antibiotic for selection of plant transformation. After four weeks numerous calli derived from at least five different Ws and rat5 plants were stained with X-gluc. Of the Ws calli sampled, 92±12% showed large blue staining areas, whereas only 26±10% of the rat5 calli showed GUS activity, and most of these blue staining regions were small (FIG. 3A). These data indicate that although the rat5 mutant can transiently express the gusA gene at high levels, it fails to stabilize gusA expression.

Figure 3B:
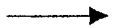

Suspension cell lines were generated from these Ws and rat5 calli and after an additional month the amount of T-DNA was assayed (using as a hybridization probe the gusA-intron gene located within the T-DNA of pBISN1) integrated into high molecular weight plant DNA from Ws and rat5 calli (Nam et al., 1997; Mysore et al., 1998). FIG. 3B shows that although T-DNA integrated into the genome of wild-type Ws plants was easily detectable, T-DNA integrated into the rat5 genome was not. These data directly demonstrate that rat5 is deficient in T-DNA integration. To demonstrate equal loading of plant DNA in each of the lanes, the gusA probe was stripped from the blot and rehybridized the blot with an Arabidopsis phenylalanine ammonia-lyase (PAL) gene probe.

FIG. 2 shows complementation of the rat5 mutant and overexpression of RAT5 in wild-type Arabidopsis plants. Maps of the binary vectors pKM4 (A) and pKM5 (B). RB, T-DNA right border; LB, T-DNA left border; pAnos, nopaline synthase polyadenylation signal sequence; histone H2A, coding sequence of the RAT5 histone H2A gene; pH2A, promoter sequence of the RAT5 histone H2A gene; Pnos, nopaline synthase promoter; hpt, hygromycin resistance gene; pAg7, agropine synthase polyadenylation signal sequence; uidA, promoterless gusA gene. Arrows above the histone H2A, uidA, and hpt genes indicate the direction of transcription. (C) Complementation of the rat5 mutant. rat5 mutant plants were transformed with an Agrobacterium strain containing the binary vector pKM4 (At1012). Hygromycin-resistant transgenic plants were obtained and were self-pollinated to obtain T2 plants. Sterile root segments of T2 plants expressing RAT5, wild-type Ws plants, and rat5 mutant plants were infected with the tumorigenic strain *A. tumefaciens* At1012. Two days after cocultivation, the roots were moved to MS medium lacking phytohormones and containing timentin. Tumors were scored after four weeks. (D) Tumorigenesis assay of Ws transgenic plants overexpressing the RAT5 histone H2A gene. Ws plants were transformed with *A. tumefaciens* At1012 containing the binary vector pKM4. Hygromycin-resistant transgenic plants were obtained and were self-pollinated to obtain T2 plants. Sterile root segments of T2 plants overexpressing RAT5 and wild-type Ws plants were infected at low bacterial density with *A. tumefaciens* A208. After two days cocultivation, the roots were moved to MS medium lacking phytohormones and containing timentin. Tumors were scored after four weeks.

Teratomas incited on the roots of these plants appeared similar to tumors generated on a wild-type plant. One of the transgenic plants tested did not recover the tumorigenesis-susceptibility phenotype, probably because of an inactive transgene. Transgenic T1 plants of rat5 obtained by transformation with At1062 (containing a genomic encoding RAT5 from the wild-type plant) were also tested for restoration of the tumorigenesis-susceptibility phenotype. Some of these plants were also able to recover the tumorigenesis-susceptibility phenotype, indicating complementation of the rat5 mutation. Hygromycin-resistant transgenic plants generated by transforming the rat5 mutant with pGPTV-HPT alone did not form tumors upon infection with *A. tumefaciens* A208.

FIG. 3 shows T-DNA integration assays of rat5 and Ws plants; (A) transient and stable GUS expression in Ws and rat5; Sterile root segments of Ws and rat5 plants were infected with the non-tumorigenic Agrobacterium strain GV3101 containing the binary vector pBISN1. Two days after cocultivation, the roots were transferred to callus inducing medium (CIM) containing timentin. Three days after infection, half of the segments were stained with X-gluc to determine the efficiency of transient GUS expression. The other group of segments was allowed to form calli on CIM. After four weeks these calli were stained with X-gluc to determine the efficiency of stable GUS expression. (B) T-DNA integration in rat5 and Ws plants. Suspension cells were derived from the calli generated from Ws and rat5 root segments infected with the non-tumorigenic Agrobacterium strain GV3101 containing the binary vector pBISN1. The suspension cell lines were grown for three weeks (without selection for transformation) in the presence of timentin or cefotaxime to kill Agrobacterium. Genomic DNA was isolated from these cells, subjected to electrophoresis through a 0.6% agarose gel, blotted onto a nylon membrane, and hybridized with a gusA gene probe. After autoradiography, the membrane was stripped and rehybridized with a phenylalanine ammonia-lyase (PAL) gene probe to determine equal loading of DNA in each lane.

MATERIALS AND METHODS

Nucleic acid manipulation. Total plant genomic DNA was isolated according to the method of Dellaporta et al. (1983). Restriction endonuclease digestions, agarose gel electrophoresis, plasmid isolation, and DNA blot analysis were conducted as described (Sambrook et al., 1982).

Plasmid Rescue. Genomic DNA (5 μg) of rat5 was digested to completion with SalI. The digested DNA was extracted with phenol/chloroform and precipitated with ethanol. The DNA was self-ligated in a final volume of 500 μl in 1× ligation buffer (Promega) with 3 units of T4 DNA ligase at 16° C. for 16 hr. The ligation mixture was precipitated with ethanol, transformed into electrocompetent *E. coli* DH10B cells (mcrBC-; Life Technologies, Inc., Gaithersburg, Md.) by electroporation (25 μF, 200 Ω, and 2.5 kV) and plated on LB medium containing ampicillin (100 μg/ml). Ampicillin-resistant colonies were lifted onto a nylon membrane, the bacteria were lysed, and DNA was denatured in situ (Sambrook et al., 1982). A radiolabeled left border (LB) sequence (3.0 kbp EcoRI fragment of pE1461)

was used as a hybridization probe to identify a plasmid containing the LB. Positive colonies were picked and plasmid DNA was isolated. By restriction fragment analysis a plasmid containing both the LB and plant junction DNA was identified. The plant junction fragment was confirmed by hybridizing the junction fragment to wild-type plant DNA. A restriction map of this plasmid, containing the LB-plant junction DNA, was made. A 1.7 kbp EcoRI fragment that contained plant DNA plus 75 base pairs of LB sequence was subcloned into pBluescript, resulting in pE1509. This fragment was subsequently sequenced at the Purdue University sequencing center.

Growth of Agrobacterium and in vitro root inoculation of *Arabidopsis thaliana* These were performed as described previously by Nam et al. (1997).

Plant Growth Conditions Seeds of various *Arabidopsis thaliana* ecotypes were obtained from S. Leisner and E. Ashworth (originally from the Arabidopsis Stock Centre, Nottingham, UK, and the Arabidopsis Biological Resource Center, Ohio State University, Columbus, respectively). Seeds were surface sterilized with a solution composed of 50% commercial bleach and 0.1% SDS for 10 min and then rinsed five times with sterile distilled water. The seeds were germinated in Petri dishes containing Gamborg's B5 medium (GIBCO) solidified with 0.75% bactoagar (Difco). The plates were incubated initially at 4° C. for 2 days and the fro 7 days under a 16-hr-lights/8-hr-dark photoperiod at 25° C. Seedlings were individually transferred into baby food jars containing solidified B5 medium and grown for 7 to 10 days for root culture. Alternatively, the seedlings were transferred into soil for bolt inoculation.

Growth of *Agrobacterium tumefaciens* All Agrobacterium strains were grown in YEP medium (Lichtenstein and Draper, 1986) supplemented with the appropriate antibiotics (rifampicin, 10 $\mu$g/mL; kanamycin, 100 $\mu$g/mL) at 30° C. Overnight bacterial cultures were washed with 0.9% NaCl and resuspended in 0.9% NaCl a $2\times10^9$ colony-forming units per mL for in vitro root inoculation or at $2\times10^{11}$ colony-forming units per mL for bolt inoculation.

In Vitro Root Inoculation and Transformation Assays Roots grown on the agar surface were excised, cut into small segments (~0.5 cm) in a small amount of sterile water, and blotted onto sterile filter paper to remove excess water. For some experiments, excised roots were preincubated on callus-inducing medium (CIM;4.32 g/L Murashige and Skoog [MS] minimal salts [GIBCO], 0.5 g/L Mes, pH 5.7, 1 mL/L vitamin stock solution [0.5 mg/mL nicotinic acid, 0.5 mg/mL pyridoxine, and 0.5 mg/mL thyamine-HCl], 100 mg/L myoinositol, 20 g/L glucose, 0.5 mg/L 2,4-dichlorophenoxyacetic acid, 0.3 mg/L kinetin, 5 mg/L indoleacetic acid, and 0.75% bactoagar) for 1 day before cutting them into segments. Dried bundles of root segments were transferred to MS basal medium (4.32 g/L MS minimal salts, 0.5 g/L Mes, pH 5.7, 1 mL/L vitamin stock solution, 100 mg/L myoinositol, 10 g/L sucrose and 0.75% bactoagar), and 2 or 3 drops of bacterial suspension were placed on them. After 10 min, most of the bacterial solution was removed, and the bacteria and root segments were cocultivated at 25° C. for 2 days.

For transient transformation assays, the root bundles were infected with Agrobacterium strain GV3101 was used (Koncz and Schell, 1986) containing the binary vector pBISN1 (Narasimhulu et al., 1996). After various periods of time, the roots were rinsed with water, blotted on filter paper, and stained with X-gluc staining solution (50 mM NaH$_2$HPO$_4$, 10 mM Na$_2$. EDTA, 300 mM mannitol, and 2 mM X-gluc, pH 7.0) for 1 day at 37° C. For quantitative measurements of $\beta$-glucuronidase (GUS) activity, the roots were ground in a microcentrifuge tube containing GUS extraction buffer (50 mM Na$_2$HPO$_4$, 5 mM DTT, 1 mM Na$_2$ EDTA, 0.1% sarcosyl, and 0.1% Triton X-100, pH 7.0), and GUS specific activity was measured according to Jefferson et al. (1987).

To quantitate tumorigenesis, root bundles were infected with wild-type Agrobacterium strains. After 2 days, the root bundles were rubbed on the agar surface to remove excess bacteria and then washed with sterile water containing timentin (100 $\mu$g/mL). Individual root segments (initial assay) or small root bundles (5 to 10 root segments; modified assay) were transferred onto MS basal medium lacking hormones but containing timentin (100 $\mu$g/mL) and incubated for 4 weeks.

For transformation of root segments to kanamycin resistance, root bundles were inoculated with Agrobacterium strain GV3101 containing pBISN1. After 2 days, small root bundles (or individual root segments) were transferred onto CIM containing timentin (100 $\mu$g/mL) and kanamycin (50 $\mu$g/mL). Kanamycin-resistant calli were scored after 4 weeks of incubation at 25° C.

To determine stable GUS expression, roots were inoculated as given above and the root segments were transferred after 2 days to CIM containing timentin (100 $\mu$g/mL) without any selection. After 4 weeks, GUS activity was assayed either by staining with X-gluc or by measuring GUS specific activity by using a 4-methylumbelliferyl $\beta$-D galactoside (MUG) fluorometric assay, as described above.

To determine the kinetics of GUS expression, root bundles were infected, the root segments were transferred after 2 days to CIM containing timentin (100 $\mu$g/mL), and calli were grown on CIM without selection. Root bundles were assayed at various times, using a MUG fluorometric assay as described above, to measure GUS specific activity.

Construction of the binary vectors pKM4 and pKM5. The plasmid pE1509 containing the 1.7 kbp junction fragment cloned into pBluescript was digested with EcoRI to release the junction fragment. The 5' overhanging ends were filled in using the Kienow fragment of DNA polymerase I and deoxynucleotide triphosphates. The T-DNA binary vector (pE1011) pGTV-HPT (Becker et al., 1992) was digested with the enzymes SacI and SmaI, releasing the promoterless gusA gene from pGTV-HPT. The 3' overhanging sequence of the larger fragment containing the origin of replication and the hygromycin resistance gene (hpt) were removed using the 3'-5' exonuclease activity of Klenow DNA polymerase, and the resulting 1.7 kbp blunt end fragment was ligated to the blunt ends of the binary vector. A binary vector plasmid containing the 1.7 kbp fragment in the correct orientation (pAnos downstream of the histone H2A gene) was selected and named pKM4 (strain El 547).

An approximately 9.0 kbp wild-type genomic SacI fragment containing the histone H2A gene (RAT5) from a lambda genomic clone was cloned into the SacI site of the plasmid pBluescript. This 9.0 kbp SacI fragment was subsequently released from pBluescript by digestion with SacI and was cloned into the SacI site of the binary vector pGTV-HPT, resulting in the plasmid pKM5 (strain E1596). Both pKM4 and pKM5 were separately transferred by triparental mating (Ditta et al., 1980) into the non-tumorigenic Agrobacterium strain GV3101, resulting in the strains *A. tumefaciens* At1012 and At1062, respectively.

Germ-line transformation of Arabidopsis. Germ-line transformations were performed as described in (Bent and Clough, 1998). Transgenic plants were selected on B5 medium containing hygromycin (20 $\mu$g/ml).

DOCUMENTS CITED

Ballas, N. & Citovsky, V. Nuclear localization signal binding protein from Arabidopsis mediates nuclear import of Agrobacterium VirD2 protein. *Proc. Natl. Acad. Sci. USA* 94, 10723–10728 (1997).

Bent, A. F. & Clough, S. J. in *Plant Molecular Biology Manual*, (eds Gelvin, S. B. & Verma, D. P. S.) vol. 3, pp. B7/1–14 (Kluwer Academic Publishers, Netherlands, 1998).

Britt, A. B. DNA damage and repair in plants. *Annu. Rev. Plant Physiol. Plant Mol. Biol.* 47, 75–100 (1996).

Dellaporta, S. L., Wood, J., & Hicks, J. B. *Plant Mol. Biol. Rep.* 1, 19–22 (1983).

Deng W. et al. Agrobacterium VirD2 protein interacts with plant host cyclophilins. *Proc. Natl. Acad. Sci. USA* 95,7040–7045 (1998).

Ditta, G., Stanfield, S., Corbin, D., & Helinski, D. R. *Proc. Natl. Acad. Sci USA* 77, 7347–7351 (1980).

Gheysen, G., Villarroel, R. & Van Montagu, M. Illegitimate recombination in plants: A model for T-DNA integration. *Genes Dev.* 5, 287–297 (1991).

Jefferson, R. A. m Kavanagh, T. A., Bevan, M. W. GUS fusions: Beta-glucuronidase as a sensitive and versitile gene fusion marker in higher plants. *EMBO J.* 6, 391–3907 (1987).

Koncz, C. and Schell, *J. Mol. Gen. Genet.* 204, 383–396 (1986).

Lichtenstein, C. and Draper, J. Genetic engeneering of plants. In Glover, D. M. (ed.) *DNA Cloning: A Practical Approach*, vol. 2, pp. 67–119 (IRL Press, Oxford, 1986).

Matsumoto, S., Ito, Y., Hosoi, T., Takahashi, Y. & Machida, Y. Integration of Agrobacterium T-DNA into tobacco chromosome: Possible involvement of DNA homology between T-DNA and plant DNA. *Mol. Gen. Genet.* 224, 309–316 (1990).

Mysore, K. S., Yi, H. C. & Gelvin, S. B. Molecular cloning, characterization and mapping of histone H2A genes in Arabidopsis. In preparation.

Mysore, K. S. et al. Role of the *Agrobacterium tumefaciens* VirD2 protein in T-DNA transfer and integration. *Mol. Plant-Microbe Interact.* 11, 668–683 (1998).

Nam J. et al. Identification of T-DNA tagged Arabidopsis mutants that are resistant to transformation by Agrobacterium. *Mol. Gen. Genet.* 261, 429–438 (1999).

Nam, J., Matthysse, A. G. & Gelvin, S. B. Differences in susceptibility of Arabidopsis ecotypes to crown gall disease may result from a deficiency in T-DNA integration. *Plant Cell* 8, 873–886 (1997).

Narasimhulu, S. B., Deng, X.-B. Sarria, R. & Gelvin, S. B. Early transcription of Agrobacterium T-DNA genes in tobacco and maize. *Plant Cell* 8, 873–886 (1996).

Ni, M. et al. Strength and tissue specificity of chimeric promoters derived from the octopine and mannopine synthase genes. Plant J. 7, 661–676 (1995).

Offringa, R. et al. Extrachromosomal homologous recombination and gene targeting in plant cells after Agrobacterium mediated transformation. *EMBO J.* 9, 3077–3084 (1990).

Ohba, T., Yoshioka, Y., Machida, C. & Machida, Y. DNA rearrangement associated with the integration of T-DNA in tobacco: An example for multiple duplications of DNA around the integration target. *Plant J.* 7, 157–164 (1995).

Paszkowski, J., Baur, M., Bogucki, A. & Potrykus, I. Gene targeting in plants. *EMBO J.* 7, 4021–4026 (1988).

Sambrook, M. A., Fritsch, E. F., & Maniatis, T. (1982) in *Molecular cloning: A laboratory manual.* 1$^{st}$ ed. (Cold Spring Harbor Laboratory Press, Cold Spring Harbor, N.Y.)

Sheng, J. & Citovsky, V. Agrobacterium-plant cell DNA transport: Have virulence proteins, will travel. *Plant Cell* 8,1699–1710 (1996).

Tao, Y., Rao, P. & Gelvin, S. B. A plant phosphatase is involved in nuclear import of the Agrobacterium VirD2/T-DNA complex. In preparation.

Zupan, J. R. & Zambryski, P. The Agrobacterium DNA transfer complex. *Crit. Rev. Plant Sci.* 16, 279–295 (1997).

TABLE 1

Complementation of the rat5 mutant and overexpression of RAT5 in wild-type (Ws) Arabidopsis plants

| % Line[a] | Root Bundles With Tumors | Tumor morphology |
| --- | --- | --- |
| rat5 complementation with At1012 (T2 plants)[a] | | |
| Ws | 98 ± 2 | large, green |
| rat5 | 21 ± 6 | small, yellow |
| rat5 At1012-1 | 64 ± 30 | large + small, green |
| rat5 At1012-2 | 17 ± 4 | small, yellow |
| rat5 At1012-3 | 70 ± 20 | large + medium, green |
| rat5 At1012-4 | 86 ± 6 | large, green |
| rat5 At1012-5 | 82 ± 10 | large, green |
| rat5 At1012-6 | 92 ± 5 | large, green |
| Overexpression of RAT5 in Ws (T2 plants)[a,b] | | |
| Ws | 35 ± 14 | large, green |
| Ws At1012-1 | 69 ± 27 | large, green |
| Ws At1012-2 | 68 ± 25 | large, green |
| Ws At1012-3 | 64 ± 13 | large, green |
| Ws At1012-4 | 63 ± 20 | large, green |

[a]at least 5 plants were tested for each mutant and 40–50 root bundles were tested for each plant
[b]Agrobacterium was diluted to a concentration 100-fold lower than that normally used, and single root segments were separated

We claim:

1. A method for increasing Agrobacterium transformation efficiency in a host plant, the method comprising:
   (a) introducing a polynucleotide sequence encoding a plant histone H2A protein to the host plant; and
   (b) expressing the polynucleotide sequence encoding a plant histone H2A protein in the host plant in a sufficient amount to increase the transformation efficiency.

2. The method of claim 1, wherein the polynucleotide sequence encoding a plant histone H2A protein is a member of an H2A gene family of Arabidopsis.

3. The method of claim 2, wherein the member of the H2A gene family of Arabidopsis is RAT5.

* * * * *